(12) United States Patent
Ekholm et al.

(10) Patent No.: US 8,057,476 B2
(45) Date of Patent: Nov. 15, 2011

(54) HUMERAL NAIL

(75) Inventors: Carl Ekholm, Onsala (SE); Anders Jonsson, Onsala (SE); Nils Zander, Eckenförde (DE)

(73) Assignee: Stryker Trauma GmbH (DE)

( * ) Notice: Subject to any disclaimer, the term of this patent is extended or adjusted under 35 U.S.C. 154(b) by 1019 days.

(21) Appl. No.: 11/823,543

(22) Filed: Jun. 27, 2007

(65) Prior Publication Data

US 2007/0255283 A1 Nov. 1, 2007

Related U.S. Application Data

(63) Continuation of application No. 10/646,299, filed on Aug. 22, 2003, now Pat. No. 7,247,156.

(30) Foreign Application Priority Data

Aug. 28, 2002 (DE) ................ 202 13 166 U

(51) Int. Cl.
*A61B 17/58* (2006.01)
(52) U.S. Cl. ........................... 606/64; 606/62
(58) Field of Classification Search .......... 606/60, 606/62–64
See application file for complete search history.

(56) References Cited

U.S. PATENT DOCUMENTS

| | | | |
|---|---|---|---|
| 4,475,545 A | 10/1984 | Ender et al. | |
| 4,622,959 A * | 11/1986 | Marcus | 606/64 |
| 5,066,296 A | 11/1991 | Chapman et al. | |
| 5,163,961 A | 11/1992 | Harwin | |
| 5,248,313 A | 9/1993 | Greene et al. | |
| 5,356,410 A | 10/1994 | Pennig et al. | |
| 5,472,444 A * | 12/1995 | Huebner et al. | 606/64 |
| 5,480,402 A * | 1/1996 | Kim | 606/64 |
| 5,489,284 A | 2/1996 | James et al. | |
| 5,549,610 A | 8/1996 | Russell et al. | |
| 5,766,174 A * | 6/1998 | Perry | 606/62 |
| 5,776,194 A | 7/1998 | Mikol et al. | |
| 6,210,414 B1 * | 4/2001 | Lin | 606/64 |
| 6,228,086 B1 * | 5/2001 | Wahl et al. | 606/67 |
| 6,270,499 B1 | 8/2001 | Leu et al. | |

(Continued)

FOREIGN PATENT DOCUMENTS

DE 19945611 9/2001

(Continued)

OTHER PUBLICATIONS

Howmedica Alta Modular Trauma System, Decades of internal fixation research embodied in one comprehensive trauma system, Apr. 1993, pp. 1-8.

(Continued)

*Primary Examiner* — Eduardo C Robert
*Assistant Examiner* — Ellen C Hammond
(74) *Attorney, Agent, or Firm* — Lerner, David, Littenberg, Krumholz & Mentlik, LLP

(57) ABSTRACT

A humeral nail for the surgical care of fractures of the proximal humerus, with a shaft which has a longitudinal axis and is provided in a proximal portion with at least transverse bores spaced apart in the axial direction. The axis of the three bores is circumferentially offset in respect to each other in planes perpendicular to the longitudinal axis of the shaft. The nail is provided with at least two additional transverse bores in a portion located towards the distal end of the nail, the proximal transverse bore running diagonally to the longitudinal axis and being located in the same plane as is the axis of the additional transverse bores.

19 Claims, 2 Drawing Sheets

U.S. PATENT DOCUMENTS

| | | | |
|---|---|---|---|
| 6,358,250 B1 | 3/2002 | Orbay | |
| 6,461,360 B1 * | 10/2002 | Adam | 606/67 |
| 6,702,816 B2 * | 3/2004 | Buhler | 606/62 |
| 6,706,046 B2 * | 3/2004 | Orbay et al. | 606/62 |
| 6,783,529 B2 * | 8/2004 | Hover et al. | 606/62 |
| 7,247,157 B2 * | 7/2007 | Prager et al. | 606/64 |
| 7,410,488 B2 * | 8/2008 | Janna et al. | 606/62 |
| 2002/0099379 A1 * | 7/2002 | Adam | 606/67 |
| 2003/0069581 A1 * | 4/2003 | Stinson et al. | 606/62 |
| 2005/0055023 A1 * | 3/2005 | Sohngen et al. | 606/62 |

FOREIGN PATENT DOCUMENTS

| | | |
|---|---|---|
| EP | 0 355 411 | 2/1990 |
| EP | 0715832 | 6/1996 |
| EP | 0853923 | 7/1998 |
| WO | WO-99/35989 | 7/1999 |

OTHER PUBLICATIONS

Richard F. Kyle, M.D., Zimmer® M/DN® Tibial and Humeral Nail Intramedullary Fixation, © 1998, 2000, 2003, pp. 1-24.

* cited by examiner

HUMERAL NAIL

CROSS REFERENCE TO RELATED APPLICATION

This application is a continuation of U.S. application Ser. No. 10/646,299, filed on Aug. 22, 2003, the disclosure of which is incorporated herein by reference.

BACKGROUND OF THE INVENTION

The invention is related to a bone nail having a plurality of transverse bores at one end thereof. More particularly, it relates to a humeral nail having a plurality of holes being angularly offset, both in a plane perpendicular to the nail axis and at an angle to that plane. It is known that fractures of the humerus often occur in the proximal region, particularly in the head region of the humerus. For the surgical care of such fractures, it is already known to provide a so-called locking nail. Preferably, the nail is driven into the humeral channel from the proximal to the distal direction. The nail is provided with locking bores in the proximal region as well in the distal region, through which bone screws are guided in order to secure the locking nail against axial dislocation and torsion. The bone screws in the proximal region serve also for the fixing of bone fragments.

A humeral nail of the described type has become known from U.S. Pat. No. 5,472,444. This nail is provided with an oblong shaft and has four transverse bores in the proximal region, which bores are disposed axially spaced apart and angularly offset from each other, in the circumferential direction. The nail shaft is also bent.

SUMMARY OF THE INVENTION

The present invention has as one object to improve a humeral nail of the type described in U.S. Pat. No. 5,472,444 to the effect that an even more effective guiding of the nail or the fracture fragments, respectively, can take place.

In the humeral nail of the present invention, the proximal transverse bore, i.e. that one which is situated closest to the proximal end, has an axis disposed diagonally to the longitudinal axis of the nail shaft.

In a humeral nail inserted in the proximal direction into the humerus, the nail sits on the outer side of the humerus head, and the transverse bores in the proximal portion are arranged such that the locking screws can be screwed into the humeral head from different directions. In the inventive nail, the diagonal arrangement of the proximal most transverse bore is such that the bone screw is screwed in from the outside towards the inside diagonally downwardly (distally). Through this, the bone screw is arranged in an anatomically more favorable fashion, because by doing so the transmission of force to the nail is configured in a more favorable manner. In addition, the bone screw can obtain a greater length, because it can be put into the humeral head across a greater length. Thus, added together, the surgical care of fractures in the head region of the humerus is improved by the features of the nail of the present invention.

According to one embodiment of the invention, the inclination of the axis of the proximal most transverse bore with respect to the longitudinal axis of the nail shaft is at an angle of about 80°.

As already mentioned, several transverse bores are provided in the proximal portion of the nail shaft. According to one embodiment, the axis of the distal most transverse bore in the proximal portion, i.e. that transverse bore which has the greatest distance from the proximal end of the nail shaft, is also disposed diagonally with respect to the longitudinal axis of the nail shaft. The angulation is such that the axis of the proximal and the distal transverse bores converge and diverge, respectively. Preferably, the bores are directed into opposite directions, i.e. one angled upwardly and one downwardly. This measure, too, proves to be extremely advantageous in fractures of the humeral head, because even here the bone screw can be selected to be longer and can be put into the endangered regions of the humerus head more effectively.

According to one embodiment of the invention, the angular offset of the distal transverse bore with respect to the proximal transverse bore is approximately 25°, this offset being preferably directed into the direction opposite to the offset of that one transverse bore which follows the proximal transverse bore.

Preferably, four transverse bores are provided in the proximal portion, the two middle bores preferably running with their axis perpendicular to the longitudinal axis of the nail shaft. The distal most bore in the proximal portion and the adjacent more proximal bore are circumferentially offset by about 90°.

According to another embodiment of the invention, the nail shaft can be solid rather than cannulated. According to a further embodiment of the invention, the nail has two distal bores one of the two distal transverse bores is constructed as an elongated (oblong) hole oriented parallel to the longitudinal axis in the distal region.

With a straight shaft, it is necessary that two separate humerus nails be provided for the left and the right humerus. According to one embodiment of the invention, except for the proximal most transverse bores, the remaining transverse bores are provided in a different arrangement for the left and the right nail shaft, the two arrangements being indeed similar with respect to the axial distance and the relative angular position, but being rotated by 180° with respect to the longitudinal axis.

BRIEF DESCRIPTION OF THE DRAWINGS

One example of the invention will be explained in more detail by means of drawings.

FIG. 1a is an end view of the nail of FIG. 1 in the direction of 1a-1a.

DETAILED DESCRIPTION

Figure 1:
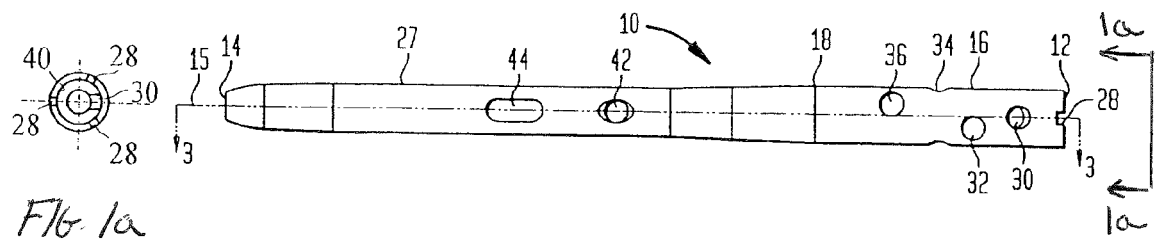
FIG. 1 shows the longitudinal view of a humeral nail for the right humerus in a side view.

Referring to FIGS. 1 to 5, there is shown a preferred humeral nail 10 for the right humerus 11. It has a straight shaft with a proximal end 12 and a distal end 14. The nail 10 is put into the humerus 11 from the proximal direction and serves for the surgical care of fractures in the proximal region of the humerus 11. The nail 10 is constructed as a locking nail having cross-bores for receiving locking screws.

The nail shaft has a longitudinal axis 15 and has a proximal portion 16, which extends distally to a cross-section 18. In the preferred embodiment, the proximal portion 16 has a constant diameter. Beginning with cross-section 18, which can be preferably formed as a relatively smooth transition, a relatively short conical portion 20 follows, and in turn is followed by a further conical portion 22. From cross-section 24 at the distal end of conical portion 22, the nail shaft extends up to the distal end 14 approximately with the same smaller diameter. The distal end portion 26 being again formed conically or spherically.

In the preferred embodiment, proximal end 12 is provided with three transverse slits 28 running perpendicular to the longitudinal axis of the nail shaft, which cooperate with corresponding projections in a device (not shown) for aiming and hammering in the nail. Slits 28 allow the nail 10 to be accommodated in the proper angular position by the device.

In the preferred embodiment, proximal portion 16 has four transverse bores 30, 32, 34 and 36. The axis of the middle bores 32, 34 extend perpendicular to the longitudinal axis of nail 10, but are rotated by 115° with respect to each other. In the preferred embodiment, the axis of proximal transverse bore 30 is disposed diagonally to the longitudinal axis, e.g. at an angle of approximately 80°, i.e. rotated 10° with respect to a plane perpendicular to the longitudinal axis 15. The proximal transverse bore 30 partially intersects an axial bore 40 of nail 10, which serves for the connection with the device (not shown) for insertion and aiming.

Bore 32 following as the next one to proximal bore 30 is located on the circumference offset with a certain angle of preferably 25°. This offset is easily seen in FIG. 1. The distal transverse bore 36 also runs diagonal to the longitudinal axis of the nail 10 with its axis, e.g. in an angle of 75° (i.e. rotated 15° with respect to a plane perpendicular to longitudinal axis 15) with the axis of transverse bores, 30, 36 converging and diverging, respectively on opposite sides of nail 10. In addition, the axis of distal transverse bore 36 is rotated with respect to proximal transverse bore 30 in the circumferential direction, again at approximately 25°. The rotation with respect to the transverse bore 32 takes place in the opposite direction, however, which again emerges from FIG. 1.

The transverse bores 30 to 36 serve for the accommodation of bone screws 100 and 102 in bores 30 and 36 respectively, which are screwed into the humerus head 90 via the hard outer layer of the humerus. For locating transverse bores 30 to 36, a corresponding aiming device (not shown) is required. The offset in the circumferential direction of the transverse bores with regard to each other enables the arrangement of the bone screws from out different directions, in order to provide surgical care to the corresponding fractures in the humerus head in an optimal manner. The diagonal arrangement of the transverse bores and 36 enables an even more optimal care of fractures, with better transmission of force from the bone to the nail and reversely. In addition, the diagonal arrangement of transverse bores 30 and 36 enables the use of particularly long bone screws 100 and 102 without which the danger exists that the humerus head might be pushed through. In the preferred embodiment, bores 32 to 36 are provided with a thread, which corresponds to the locking or bone screws. Through this, an unintended drifting out of the screws is prevented.

In the preferred embodiment, portion 27 of nail 10 has two transverse bores 42, 44 are provided at a relative distance to distal end 14. The axis of the bores lay in one plane in which plane the axis of the proximal transverse bore 30 is also situated. This plane contains longitudinal axis 15 of the shaft. The distally positioned distal transverse bore 44 may be in the form of an elongated hole, which can be recognized particularly from FIGS. 1 and 3. The transverse bores 42, 44 serve for the accommodation of bone screws for the bracing of nail 10 in the humerus shaft.

Figure 2:
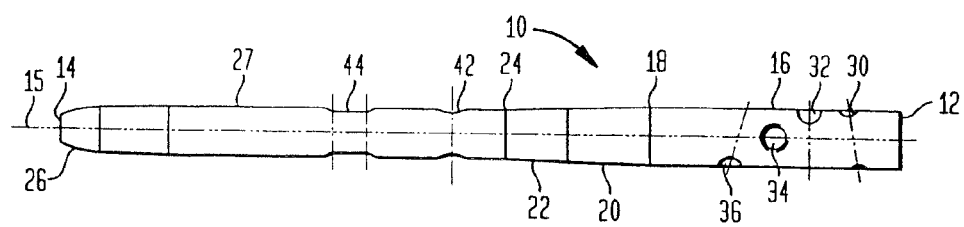
FIG. 2 shows the side view of the nail according to FIG. 1, rotated by 90°.
Figure 3:
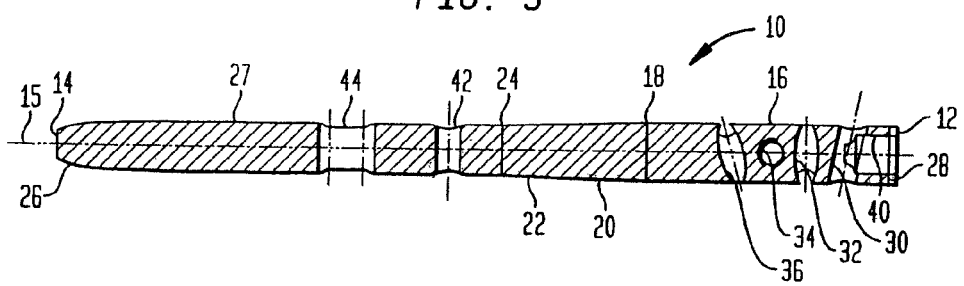
FIG. 3 shows a section through the nail according to FIG. 1 along the line 3-3.
Figure 4:
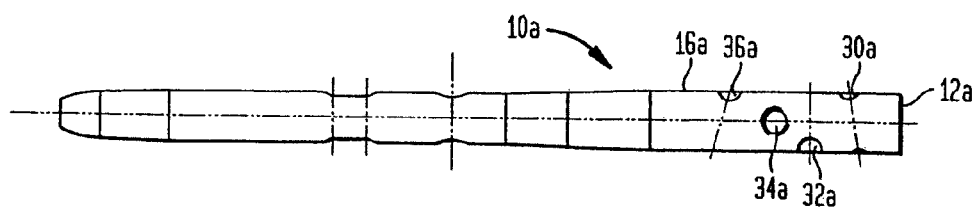
FIG. 4 shows the side view of an inventive humeral nail for the left humerus in a view analogous to FIG. 2.
Figure 5:
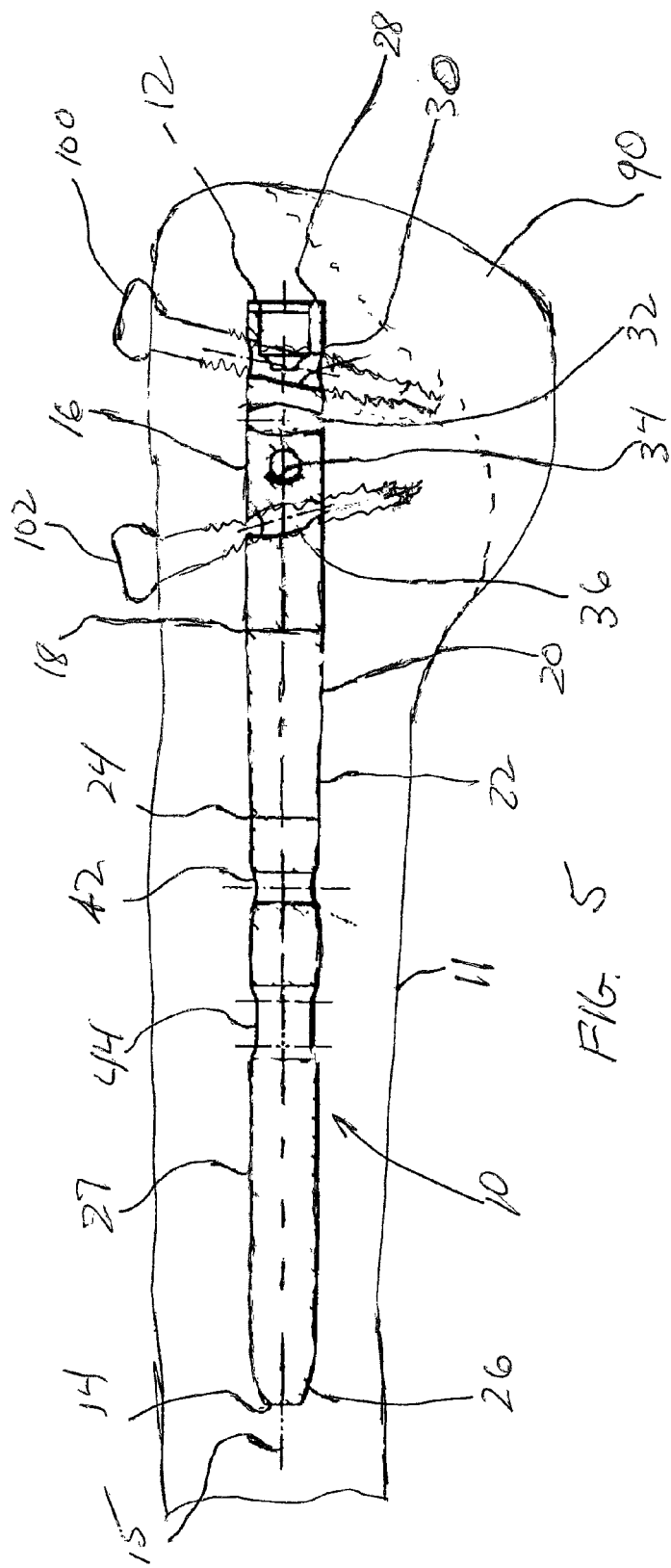
FIG. 5 shows the nail of FIG. 3 inserted in the proximal humerus including proximal and distal bone screws.

As already mentioned, nail 10 according to FIGS. 1 to 3 serves for the surgical care of fractures in the right humerus. A nail 10a for the left of the humerus is represented in FIG. 4 and the shaft is formed identically to the shaft of nail 10 according to the FIGS. 1 to 3. For that reason, the shaft will not be discussed further in detail in connection with nail 10a, except for the proximal portion 16a, which also has four transverse bores 30a, 32a, 34a and 36a. The construction of the transverse bores 30a to 36a again resembles those according to FIGS. 1 to 3. Even the position of the proximal transverse bore 30a is identical to the transverse bore 30 according to FIGS. 1 to 3. Only the arrangement of the transverse bores 32a to 36a is different to that one according to FIGS. 1 to 3, in that this arrangement is mirror-like with respect to that one according to FIG. 2. The different arrangement at nail 10a results purely from the fact that the nail 10a is used for the left humerus. Thus, with respect to the humerus to be applied, i.e. the left or right one, the arrangement of the transverse bores 30 to 36 and 30a to 36a are identical. The bores 30, 32, 34 and 36 for either the left or right versions may be threaded to correspond to the threads of a locking screw. The nail shaft 10, 10a may either be straight or curved. If the nail is curved, then the angular relationships would be with respect to the longitudinal axis at that part of the shaft, i.e. proximal or distal.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

The invention claimed is:

1. A humeral nail for the proximal humerus having first and second ends comprising a solid shaft having a proximal nail portion adjacent the first nail end and a distal nail portion adjacent the second end of the nail, the proximal nail portion having a longitudinal axis and at least three axially spaced completely threaded transverse bores, a bone screw having an end with a head and a threaded shaft received in each threaded bore each bore having an axis, which axes are circumferentially angularly offset from each other about the longitudinal axis of the proximal nail portion, at least two of the proximal transverse bores having a bore axis which extends at a non-perpendicular proximal-distal angle to the longitudinal axis of the proximal nail portion and at least one bore axis extends perpendicularly to the longitudinal axis of the proximal nail portion, a bore axis of a proximal bore of the non-perpendicular bores angled toward the first end and a bore axis of a distal bore of the non-perpendicular bores angled toward the second end, the bore axes of the first and second non-perpendicular bores lying in non-parallel planes the threaded shaft of the bone screw in the proximal bore angled towards a humeral head in a proximal to distal direction and the threaded shaft of the bone screw in the distal bore angled toward the humeral head in a distal to proximal direction.

2. The humeral nail as set forth in claim 1 wherein the axis of the proximal most transverse bore extends at a proximal to distal angle to the proximal nail portion longitudinal axis.

3. The humeral nail as set forth in claim 2 wherein the axis of the distal most transverse bore in the proximal portion runs at a proximal-distal angle to the longitudinal axis of the proximal nail portion oriented with respect to the angle of the proximal most hole axis such that the axes of the proximal and distal transverse bores converge.

4. The humeral nail as set forth in claim 3 wherein the axis of the distal most transverse bore is at an angle of approximately 75° to the longitudinal axis of the proximal nail portion and the angle of the proximal most hole is approximately 80°.

5. The humeral nail as set forth in claim 4 wherein the circumferential angular offset between the distal most transverse bore with respect to the proximal most transverse bore is approximately 25°.

6. The humeral nail as set forth in claim 1 wherein four transverse bores are provided in the proximal portion of the nail shaft.

7. The humeral nail as set forth in claim 6 wherein the transverse bore adjacent the proximal most transverse bore is oriented with its axis approximately perpendicular to the proximal nail portion longitudinal axis.

8. The humeral nail as set forth in claim 6 wherein the transverse bore adjacent the most distal transverse bore in the proximal portion is oriented with its axis approximately perpendicular to the proximal nail portion longitudinal axis.

9. The humeral nail as set forth in claim 6 wherein the angular offset between the transverse bore adjacent the proximal most transverse bore and the proximal most bore is approximately 25°.

10. The humeral nail as set forth in claim 9 wherein the angular offset between the transverse bore adjacent the distal most bore and the distal most bore in the proximal portion is approximately 90°.

11. The humeral nail as set forth in claim 10 wherein the angular offset of the two bores adjacent the proximal most transverse bore and the distal most transverse bore is 90°.

12. The humeral nail as set forth in claim 6 wherein the shaft has a distal portion with two transverse bores, the distal most transverse bore is formed as an elongated hole elongated in a direction parallel to a longitudinal nail axis in the distal region.

13. The humeral nail as set forth in claim 1 wherein the thread of the transverse bores corresponds to the thread of a locking screw.

14. A nail for insertion into a long bone having first and second ends with a longitudinal axis extending between said first and second ends comprising:
a solid shaft having a first portion adjacent the first end, the first portion having a longitudinal axis;
at least three completely threaded cross-bores located in the first portion adjacent the first end, each of the cross-bores having a bore axis oriented at a different circumferential angle with respect to the longitudinal axis and at least two of said cross-bores having a bore axis lying in non-parallel planes and oriented at non-perpendicular angles with respect to the longitudinal nail axis and one cross-bore extending perpendicular to the longitudinal axis;
at least one cross-bore located in a second nail portion adjacent said second end; and
a first bone screw having a head and a threaded shaft extending through a proximal most bore of the at least three bores and a second bone screw extending through a distal most bore of the at least three bores, the threaded shaft of the first bone screw angled towards a humeral head in the proximal to distal direction and the threaded shaft of the second bone screw angled toward the humeral head in a distal to proximal direction.

15. The nail as set forth in claim 14 wherein the axis of an intermediate cross-bore of the at least three cross-bores adjacent the first end is oriented perpendicular to said longitudinal axis.

16. The nail as set forth in claim 14 wherein there are four cross-bores located adjacent the first end.

17. The nail as set forth in claim 16 wherein the nail axes of two cross-bores of the four cross-bores are oriented perpendicular to the longitudinal axis.

18. The nail as set forth in claim 14 wherein the axes of the at least one cross-bar adjacent said second end lies in the same plane as a plane containing the axis of the cross-bore closest to the first end of the nail.

19. The nail as set forth in claim 14 wherein the axes said at least two cross-bores oriented at a non-perpendicular axis to the longitudinal axis are oriented at diverging angles.

* * * * *